(12) United States Patent
Zhang et al.

(10) Patent No.: US 10,169,870 B2
(45) Date of Patent: Jan. 1, 2019

(54) OBJECTIVE METHOD FOR ASSESSING HIGH CONTRAST RESOLUTION OF IMAGE BASED ON RAYLEIGH CRITERION AND TESTING OPERATING METHOD

(71) Applicant: NATIONAL INSTITUTE OF METROLOGY, CHINA, Beijing (CN)

(72) Inventors: Pu Zhang, Beijing (CN); Wenli Liu, Beijing (CN)

(73) Assignee: NATIONAL INSTITUTE OF METROLOGY, CHINA, Beijing (CN)

( * ) Notice: Subject to any disclaimer, the term of this patent is extended or adjusted under 35 U.S.C. 154(b) by 109 days.

(21) Appl. No.: 15/379,697

(22) Filed: Dec. 15, 2016

(65) Prior Publication Data
US 2017/0193656 A1    Jul. 6, 2017

(30) Foreign Application Priority Data
Dec. 15, 2015   (CN) .......................... 2015 1 0926662

(51) Int. Cl.
*G06K 9/00*    (2006.01)
*G06T 7/00*    (2017.01)
(Continued)

(52) U.S. Cl.
CPC ............ *G06T 7/0012* (2013.01); *A61B 6/032* (2013.01); *A61B 6/58* (2013.01); *A61B 6/583* (2013.01);
(Continued)

(58) Field of Classification Search
None
See application file for complete search history.

(56) References Cited

U.S. PATENT DOCUMENTS

| | | | | |
|---|---|---|---|---|
| 5,117,445 A | * | 5/1992 | Seppi | A61B 6/032 378/19 |
| 2009/0092227 A1 | * | 4/2009 | David | A61B 6/4233 378/36 |
| 2015/0150526 A1 | * | 6/2015 | Ohishi | A61B 6/463 378/62 |

OTHER PUBLICATIONS

American Association of Physicists in Medicine. "Specification and Acceptance Testing of Computed Tomography Scanners". Report of Task Group 2: Diagnostic X-Ray Imaging Committee. AAPM Report No. 39. American Institute of Physics (1993): 1-95.
(Continued)

*Primary Examiner* — Wei Wen Yang
(74) *Attorney, Agent, or Firm* — Caesar Rivise, PC (57) ABSTRACT

The present invention relates to a novel objective method for assessing high contrast resolution of images based on Rayleigh criterion and a testing operating method. The novel objective method for assessing high contrast resolution of images based on Rayleigh criterion involves combining the Rayleigh criterion with regional pixel intensity profiles for simultaneous application to high contrast resolution images of CT equipment, which allows objective assessment by using the Rayleigh criterion after the drawing of the regional pixel intensity profiles; the introduction of a normalized margin and the use of a Lanczos window function for interpolation processing on original images enable a considerably practical, time-effective and operable objective assessment method that is convenient for testers to use and also easy for CT equipment operators to use. Such a method, just like a modulation transfer function (MTF) method, is capable of tracking subtle and slow changes of the high contrast resolution of CT equipment in the life cycle thereof objectively and accurately, thus allowing improvement of the use efficiency of the CT equipment in the life cycle
(Continued)

thereof; therefore, the method is suitable for extensive popularization and application.

21 Claims, 7 Drawing Sheets

(51) Int. Cl.
    *A61B 6/00*     (2006.01)
    *A61B 6/03*     (2006.01)
    *G06T 3/40*     (2006.01)
    *G06T 5/50*     (2006.01)
    *H04N 1/00*     (2006.01)
    *H04N 17/00*     (2006.01)

(52) U.S. Cl.
    CPC ............ *A61B 6/586* (2013.01); *G06T 3/4007* (2013.01); *G06T 5/50* (2013.01); *H04N 1/00026* (2013.01); *G06T 2207/10081* (2013.01); *G06T 2207/20224* (2013.01); *H04N 17/00* (2013.01)

(56) References Cited

OTHER PUBLICATIONS

Bissonnette et al. "A quality assurance program for image quality of cone-beam CT guidance in radiation therapy." Medical physics 35.5 (2008): 1807-1815.

Boone et al. "Determination of the presampled MTF in computed tomography." Medical Physics 28.3 (2001): 356-360.

Chen et al. "Assessment of volumetric noise and resolution performance for linear and nonlinear CT reconstruction methods." Medical physics 41.7 (2014): 071909:1-071909:12.

Dobeli et al. "Optimization of computed tomography protocols: limitations of a methodology employing a phantom with location-known opacities." Journal of digital imaging 26.6 (2013): 1001-1007.

Droege et al. "A practical method to measure the MTF of CT scanners." Medical physics 9.5 (1982): 758-760.

Hungler et al. "Comparison of Image Filters for Low Dose Neutron Imaging." Physics Procedia 43 (2013): 169-178.

Mutic et al. "Quality assurance for computed-tomography simulators and the computed-tomography-simulation process: Report of the AAPM Radiation Therapy Committee Task Group No. 66." Medical physics 30.10 (2003): 2762-2792.

Samei et al. "A method for measuring the presampled MTF of digital radiographic systems using an edge test device." Medical physics 25.1 (1998): 102-113.

Steiding et al. "A quality assurance framework for the fully automated and objective evaluation of image quality in cone-beam computed tomography." Medical physics 41.3 (2014): 031901:1-031901:15.

Zhang et al. "A novel objective method for assessing high-contrast spatial resolution in CT based on the Rayleigh criterion." Medical Physics 44.2 (2017): 460-469.

\* cited by examiner

OBJECTIVE METHOD FOR ASSESSING HIGH CONTRAST RESOLUTION OF IMAGE BASED ON RAYLEIGH CRITERION AND TESTING OPERATING METHOD

This application claims priority under 35 U.S.C. § 119 to Chinese Application 201510926662.6 filed on Dec. 15, 2015 which is hereby incorporated by reference in its entirety.

FIELD OF THE INVENTION

The present invention relates to a testing method for regular quality assessment (QA) on CT equipment in the field of methods for assessing medical diagnostic machines, and in particular to a novel objective method for assessing high contrast resolution of images based on Rayleigh criterion. The introduction of a normalized margin (N) and the use of a Lanczos window function for interpolation processing on original images allow a pixel intensity profile method based on the Rayleigh criterion to be a considerably practical, time-effective and operable objective assessment method that is suitable for extensive popularization and application.

BACKGROUND OF THE INVENTION

Figure 1:
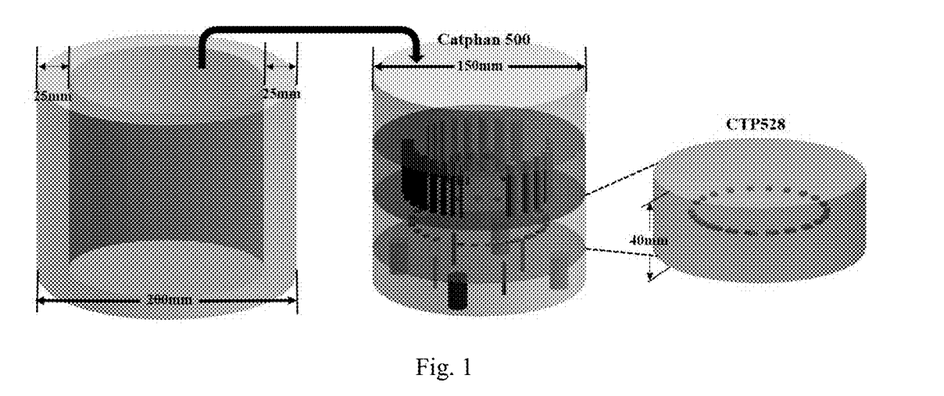
FIG. 1 illustrates a Catphan 500 phantom of the present invention. An external portion, an internal portion, and a high contrast resolution testing module CTP528 are shown.

Medical CT equipment must undergo regular quality assessment (QA) testing to ensure the effective use thereof. Phantoms are commonly used tools for QA testing on CT equipment. The Catphan® 500 phantom (The Phantom Laboratory, Salem, N.Y., USA) is widely used in China, because it is recommended by China's existing verification regulation. The Catphan 500 phantom is mainly suitable for axial scanning of heads in size and function, and contains four testing modules therein, as shown in FIG. 1a and FIG. 1b. The Catphan 500 phantom is mainly composed of four testing modules that are used for testing image uniformity, low contrast resolution, high contrast resolution, and computed tomography (CT) number linearity, respectively. The high contrast resolution describes the capability of an imaging device to distinguish tightly close objects, and is also an important index for image performance in QA testing. In the Catphan 500 phantom, the high contrast resolution testing module CTP528 with an epoxy background is mainly composed of 21 aluminum line pair groups and 2 tungsten bead point sources (used for a point spread function (PSF) method) each having a diameter of 0.28 mm. The 21 line pair groups in the CTP528 module are arranged annularly. Each line pair group is expressed in the form of line pairs per centimeter (LP/cm), as shown in FIG. 1(c). One LP group consists of one or more pairs of black and white stripes having the same size, which represent (1-21) LP/cm, respectively. The PSF method has the advantages of simple structure and easy data processing, and the disadvantages of small data size, being seriously affected by noise, poor data reproducibility, and especially great difference between calculation results before and after image filtering.

A visual inspection method for high contrast resolution assessment presented in China's existing verification regulation is as follows: the window width (WW) of CT equipment is adjusted to be approximate to the minimum, and the window level (WL) of the CT equipment is adjusted to allow visual recognition of the smallest LP group. Such a visual inspection method is simple and fast, but has assessment results completely depending on the subjective consciousness of testers, with poor reproducibility and high uncertainty. In addition, in actual field tests, most of testers have insufficient experience, which further exacerbates the uncertainty of the test results.

In addition to the subjective assessment method, it is also presented in China's existing verification regulation that the built-in modulation transfer function (MTF) software of CT equipment under test is used for objective assessment. However, CT equipment from different manufactures almost all has their unique modulation transfer function (MTF) testing programs, which are difficult to standardize. The process of calling a program will certainly take up the running time of a machine, which causes a great trouble for QA testing. In spite of this, the MTF is always accepted as the gold standard for objective assessment on high contrast resolution in imaging systems; nevertheless, common image processing software hardly meets the use requirement of such a method on accurate positioning due to the annular structure of the CTP528 module. Therefore, the MTF method is poor in both operability and time efficiency.

Furthermore, in China, especially in large third-grade class-A hospitals, CT equipment may be used each day from dozens of times up to a hundred and even hundreds of times. Then, the performance of the CT equipment certainly declines gradually with the increase of exposures. According to the provisions of the verification regulation, the period of verification for CT equipment in use is one year; then, the high contrast resolution capability of medical CT equipment certainly changes, but this change is certainly accumulated over a long period. In the past, if a user of certain CT equipment wants to clearly control the change conditions of this CT equipment, the user needs to regularly draw an MTF curve by use of the MTF method and regard the value of the horizontal coordinate corresponding to the intersection point of the MTF curve and a threshold $MTF_{10\%}$ as the high contrast resolution for this CT equipment. However, such a method is too difficult to operate, resulting in that a tester fails in testing at set time, and the CT equipment operators also cannot test the CT equipment.

In short, the subjective visual inspection method has excellent time efficiency, but is poor in accuracy and reproducibility, and the MTF method is good in both accuracy and reproducibility, but poor in operability and time efficiency.

In view of the defects of the above existing testing method for assessing the high contrast resolution, the inventor has made continuous research in order to create a novel objective method for assessing high contrast resolution of images based on Rayleigh criterion and make the method more practical.

SUMMARY OF THE INVENTION

A major objective of the present invention is to overcome the defects in the existing testing method for assessing high contrast resolution and provide a novel objective method for assessing high contrast resolution of images based on Rayleigh criterion and a testing operating method. The technical problem to be solved is to enable an objective method for assessing the high contrast resolution having good accuracy, reproducibility and time efficiency to be capable of greatly improving the working efficiency of a QA tester and very suitable for use in practice while ensuring accurate and reliable testing results.

A further major objective of the present invention is to provide a novel objective method for assessing high contrast resolution of images based on Rayleigh criterion and a testing operating method that are made to track a subtle and slow change of high contrast resolution of CT equipment in the life cycle thereof objectively and accurately just like the MTF method, thus allowing improvement of the use efficiency of the CT equipment in the life cycle thereof.

The objectives of the present invention and the technical problems thereof are implemented and solved by using the following technical solutions. A novel objective method for assessing high contrast resolution of images based on Rayleigh criterion provided according to the present invention includes the following steps.

Step 1, a Regional Pixel Intensity Profile Method Based on the Rayleigh Criterion The Rayleigh criterion is combined with a regional pixel intensity profile for simultaneous application to a high contrast resolution image of CT equipment, wherein objective assessment is carried out using the Rayleigh criterion after the drawing of regional pixel intensity profiles, i.e., judging a line pair group resolution capability by visually inspecting the shape fluctuation of the regional pixel intensity profiles of regions of interest (ROIs), followed by the objective assessment by using the Rayleigh criterion. A basic method of the Rayleigh criterion is that when two diffraction fringes formed by two light sources on an image plane of an optical instrument are combined into a wide fringe, the two fringes are just distinguishable from each other when an irradiance at the center of the wide fringe or a lowest amplitude is $8/\pi^2$ (i.e., 0.81)×a maximum irradiance.

Step 2, Interpolation Processing on an Original Image

The use of an interpolation algorithm allows great improvement of overlapping of original adjacent pixel points and enhancement of the consistency of middle three lines of pixel intensity profiles in each line pair group under the circumstance of ensuring complete information of the original image.

Step 3, Definition of Normalized Margin (1) Determination of Ratio R

Although the use condition for the Rayleigh criterion is two isolated point light sources equivalent in intensity, each aluminum strip through which the regional pixel intensity profile passes can be also viewed as a point source due to very small size of the line pair groups and the regional pixel intensity profile reflecting the local information of each line pair group. Since most line pair groups are each composed of 4 or 5 line pairs, for the regional pixel intensity profile of a certain line pair group, the epoxy background having a CT (computed tomography) number of about (100-120) HU needs to be subtracted to avoid interference. Therefore, the minimum pixel intensity and the maximum pixel intensity are equal to the average amplitude of these line pairs minus the background. In other words, when the ratio R of the minimum pixel intensity to the maximum pixel intensity is not above 81%, the line pair group is regarded as being distinguishable.

(2) Definition of Margin

When the ratio R=the minimum pixel intensity÷the maximum pixel intensity is very close to 81% and the assessment result is at the integer level, it is necessary to define the margin: M=80%−R", wherein M is the margin;

R" is a first ratio on a R curve for the CT equipment that is just below 80%;

CT equipment $E_1$ and CT equipment $E_2$ with significant differences in high contrast resolution capability are selected, and the ratios R of (1-10) LP groups of the CT equipment $E_1$ and the CT equipment $E_2$ are connected into piecewise lines, defined as ratio $R_1$ and ratio $R_2$, respectively; the ratio R being between 80% and 81% indicates that the high contrast resolution for a certain piece of equipment is between two adjacent line pair groups; the ratio $R_{1'}$ of the CT equipment $E_1$ is very close to the critical value 81%, which indicates that the high contrast resolution for the CT equipment $E_1$ is certainly between the high contrast resolution $C_1$ and the high contrast resolution $C_{1'}$ and more close to the high contrast resolution $C_{1'}$.

(3) Further Definition of Normalized Margin

The normalized margin is further defined in order to improve the accuracy of measurement results, i.e., to enable measurement results to be accurate at the decimal level just like the MTF method under the premise of ensuring the effectiveness: N=M/D, where distance D=R'−R", wherein M is the margin;

R" is the first ratio;

R' is a second ratio on the R curve for the CT equipment that is just above 80%.

Step 4, Comparative Assessment

In the case that the high contrast resolutions C of line pair groups corresponding to the last ratios R below 80% in different ratio R curves are the same, the normalized margins N corresponding to the integer-level high contrast resolutions C are compared. The larger the value of the normalized margin, the higher the high contrast resolution C for the CT equipment.

When the margin$_{E1}$ of the CT equipment $E_1$ is equal to 80%−$R_1$, the normalized margin $N_{E1}$ of the CT equipment $E_1$ is equal to margin$_{E1}$/distance$_{E1}$, and the distance$_{E1}$ is equal to $R_{1'}$−$R_1$, the high contrast resolution $C_{E1}$ for the CT equipment $E_1$ is equal to $C_1$+$N_{E1}$. Because the normalized margin is a value between 0 and 1, a greater value represents that the high contrast resolution for the CT equipment $E_1$ is closer to ($C_1$+1) LP/cm.

For the CT equipment $E_2$, the high contrast resolution $C_2$ corresponding to the last pixel intensity profile ratio $R_2$ below 81% is equal to 4LP/cm according to the Rayleigh criterion. The margin$_{E2}$ is equal to 80%−$R_2$ and is not zero, and the high contrast resolution for the CT equipment $E_2$ is between the high contrast resolution $C_2$ and the high contrast resolution $C_{2'}$; similarly, the normalized margin $N_{E2}$ of the CT equipment $E_2$ is equal to margin$_{E2}$/distance$_{E2}$; then, the high contrast resolution $C_{E2}$ for the CT equipment $E_2$ is equal to $C_2$+$N_{E2}$.

(2) When the high contrast resolutions of two pieces of equipment are at the same integer level, more detailed comparison can be made by comparing the normalized margins of the two pieces of equipment at this integer level; the larger the normalized margin, the higher the high contrast resolution for the CT equipment.

(3) If the two pieces of equipment have their normalized margins very close to each other at the same high contrast resolution level, comparison needs to be made to the area defined by the ratio R curve, the last ratio R below 80% and the high contrast resolution C for each equipment; the larger the area, the worse the high contrast resolution.

As for the novel objective method for assessing high contrast resolution of images based on Rayleigh criterion as described above, the interpolation method in step 2 is using a Lanczos window function for interpolation processing on an original image.

As for the novel objective method for assessing high contrast resolution of images based on Rayleigh criterion as described above, the step (4) is simplified to calculate only a last ratio R below 80% and a first ratio R of 80% or above.

A testing operating method on CT equipment according to the novel objective method for assessing high contrast resolution of images based on Rayleigh criterion as described above includes the following steps:

Step 1, Interpolation Processing a tester performs interpolation processing on a high contrast resolution image of CT equipment to be tested using image processing tool software having the interpolation processing and regional pixel intensity profile functions;

Step 2, Visual Inspection Distinguishing after the interpolation, the tester finds out the region of the high contrast resolution through visual inspection; the last line pair group that can be clearly distinguished as being not sticking, connected and broken through visual inspection by adjusting a window width (WW) and a window level (WL), and the first line pair group that may not be distinguished through visual inspection; it is above 90% possibility that only regional pixel intensity profile assessment based on Rayleigh criterion needs to be continuously made for the two line pair groups using commercial image processing tool software and corresponding ratios R are calculated; if the ratios R of the two line pair groups do not satisfy the use condition as described above, it only needs to make the regional pixel intensity profile assessment based on Rayleigh criterion for one more line pair group;

Step 3, Calculation of Normalized Margin the tester calculates the normalized margin according to the normalized margin formula in step 3 of claim 1 to obtain the final high contrast resolution that can be accurate to the decimal level;

Step 4, Comparative Assessment the tester makes comparative assessment according to the method in step 4 of claim 1.

Compared with the prior art, the present invention has obvious advantages and beneficial effects. The advantages are at least as follows:

1. The present invention combines the Rayleigh criterion with regional pixel intensity profile for simultaneous application to high contrast resolution images of CT, thereby enabling a simple, accurate, time-efficient and operable testing method.
2. The present invention utilizes the Lanczos window function for interpolation processing on original images, great improvement of overlapping of original adjacent pixel points and enhancement of the consistency of middle three lines of the pixel intensity profiles in each line pair group under the circumstance of ensuring complete information of the original image;
3. The present invention introduces the normalized margin (N) and uses the Lanczos window function for interpolation processing on original images, and therefore, the testing method is simple, and highly superior to the existing testing methods in time efficiency and operability.
4. The present invention allows great improvement of the working efficiency of testers due to simple, accurate, short-time and highly operable testing method. The practical effect can be exactly improved. The testing method not only is convenient to use without complex procedure, but also has value in use and is suitable for extensive popularization and utilization.
5. The present invention employs the phantom recommended in the regulation, which is simple and does not bring extra economic burden for users; thus, the present invention is good in economic benefit and suitable for use in practice.
6. The present invention is capable of tracking subtle and slow changes of high contrast resolution of CT equipment in the life cycle thereof objectively and accurately just like the MTF method, and allowing a user of CT equipment to use the present invention at any time and know the current state and performance of the CT equipment clearly and accurately. As verified, the present method has good consistency with the MTF method in testing results.

The above descriptions are merely summary of the technical solutions of the present invention. In order to more clearly know the technical means of the present invention and implement them according to the contents of the description, and to make the above and other objectives, features and advantages of the present invention more obvious and easier to understand, preferred embodiments are presented below to provide detailed descriptions in conjunction with accompanying drawings.

DESCRIPTION OF THE EMBODIMENTS

In order to further elaborate the technical means adopted in the present invention to achieve the desired objectives thereof and the produced effects, a novel objective method for assessing high contrast resolution of images based on Rayleigh criterion presented by the present invention will be described in detail below in conjunction with the accompanying drawings and preferred embodiments.

Referring to FIG. 1 to FIG. 12, a novel objective method for assessing high contrast resolution of images based on Rayleigh criterion of a preferred embodiment of the present invention mainly includes the following steps.

Step 1, a Regional Pixel Intensity Profile Method Based on the Rayleigh Criterion The Rayleigh criterion is combined with regional pixel intensity profiles for simultaneous application to a high contrast resolution image of CT equipment, wherein objective assessment is carried out using the Rayleigh criterion after the drawing of regional pixel intensity profiles, i.e., judging a line pair group resolution capability by visually inspecting the shape fluctuation of the regional pixel intensity profiles of regions of interest (ROIs), followed by the objective assessment by using the Rayleigh criterion.

Figure 2:
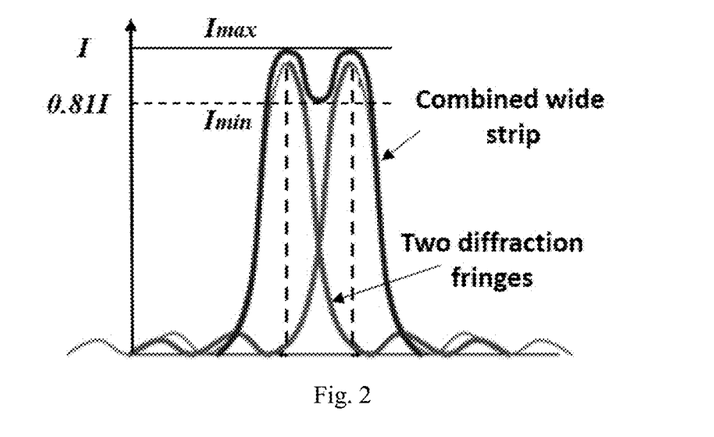
FIG. 2 is a schematic diagram of the Rayleigh criterion of the present invention.

As shown in FIG. 2, in an optical system, the Rayleigh criterion is often used as a quantitative assessment index to determine the resolution capability of an optical instrument. It is to judge the line pair group resolution capability by visually inspecting the shape fluctuation of the regional pixel intensity profiles of the regions of interest (ROIs), followed by the objective assessment by using the Rayleigh criterion. The key point of the Rayleigh criterion is that when two diffraction fringes formed by two light sources on an image plane of an optical instrument are combined into a wide fringe, the two fringes are just distinguishable from each other when the irradiance at the center of the wide fringe or the lowest amplitude is $8/\pi^2 \times$ the maximum irradiance.

Step 2, Interpolation Processing on an Original Image

In a CTP528 module, the line pair groups have a very small spatial size relative to the whole module, and occupy a small portion of a pixel value in a cross-sectional image generated by scanning under CT equipment. The size of a medical image is generally 512×512. Taking the FOV (Field of View)=245 mm used in this embodiment as an example, the size of each pixel point is approximately 0.478 mm, which is equivalent to that the high contrast resolution of an image of the medical CT equipment is about 10 LP/cm under limiting conditions. Besides, due to an annular arrangement structure, each line pair group is not completely parallel or perpendicular to the arrangement direction of the pixel points, but forms a certain angle. Hence, when regional pixel intensity profiles are created for the line pair groups, the internal boundaries of almost all the line pair groups are comparatively rough, and the adjacent pixel points severely overlap. The overlapping of the adjacent pixel points increases much difficulty to detail resolution, thus resulting in poor consistency of parallel and adjacent regional pixel intensity profiles in the line pair groups. Therefore, observers cannot determine accurate values of the minimum pixel intensity $I_{min}$ and the maximum pixel intensity $I_{max}$, and the Rayleigh criterion is unusable under these circumstances.

Since the Rayleigh criterion is unusable in the existing state, the resolution of images is increased on the premise that the image information is ensured, thus making up for deficiencies of the existing images and providing richer and smoother detail information. It costs much to increase the resolution of images by using hardware equipment. Due to the limitation of computational resources, it is generally impossible to adopt a complicated reconstruction method. Furthermore, for a CTP528 module image, the regions of interest (ROIs) are just local regions in the image, and therefore, the image interpolation method is adopted to improve the image resolution in the present invention.

After the comparison of a plurality of different interpolation algorithms as described above, it is considered that the Lanczos window has better performance than other window functions in medical image interpolation. The Lanczos window can obtain excellent interpolation results while guaranteeing distortionless images. Therefore, the optimal embodiment of the present invention uses the Lanczos window function for interpolation processing on original images.

Step 3, Definition of Normalized Margin (1) Determination of Ratio R

Figure 3:
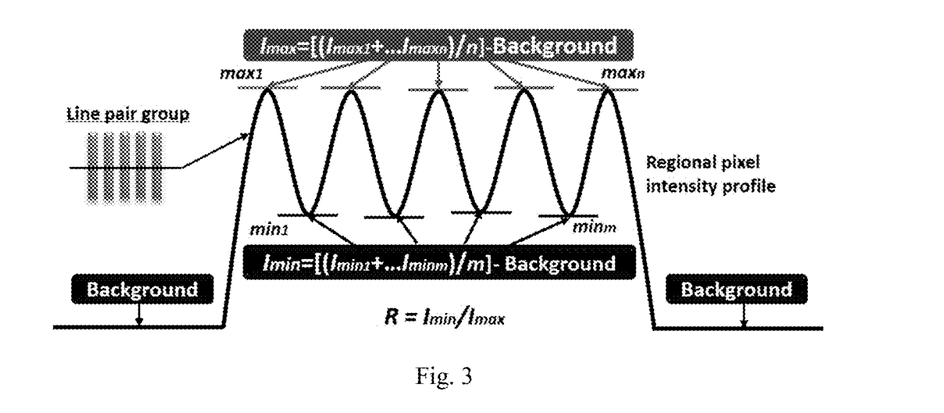
FIG. 3 is a schematic diagram of judging the resolution of line pair groups using the Rayleigh criterion.

Although the use condition for the Rayleigh criterion is two isolated point light sources equivalent in intensity, each aluminum strip through which the regional pixel intensity profile passes can be viewed approximately as a point source due to very small size of the line pair groups and the regional pixel intensity profile reflecting the local information of each line pair group. Since most line pair groups are each composed of 4 or 5 line pairs, for the regional pixel intensity profile of a certain line pair group, the epoxy background having a CT (computed tomography) number of about (100-120) HU needs to be subtracted to avoid interference. Therefore, as shown in FIG. 3, the minimum pixel intensity $I_{min}$ and the maximum pixel intensity $I_{max}$ are equal to the average amplitude of these line pairs minus the background. In other words, when the ratio R of the minimum pixel intensity $I_{min}$ to the maximum pixel intensity $I_{max}$ is not above 81%, the line pair group is regarded as being distinguishable.

(2) Definition of Margin

The assessment method in step 3 (1) has two apparent problems: first, the final result is difficult to confirm when the ratio R is very close to 81%; second, the assessment result can only be at the integer level. Aiming at this situation, it is necessary to define the concept of margin: M=80%−R″, wherein M is the margin;

R″ is a first ratio on a R curve for the CT equipment that is just below 80%.

Figure 4:
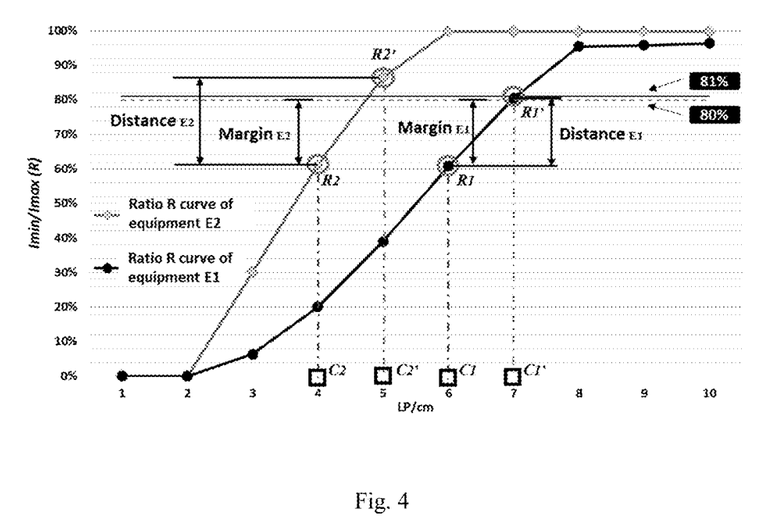
FIG. 4 is a schematic diagram of further improving the accuracy of assessment results of the Rayleigh criterion.

As shown in FIG. 4, CT equipment $E_1$ and CT equipment $E_2$ with significant differences in high contrast resolution capability were selected, and the ratios R of (1-10) LP/cm LP groups of the CT equipment $E_1$ and the CT equipment $E_2$ were connected into piecewise lines, defined as ratio $R_1$ and ratio $R_2$, respectively. Based on lots of experiments, it is proved that the ratio R being between 80% and 81% indicates that the high contrast resolution C for a piece of equipment is between two adjacent line pair groups. By taking the ratio R of the CT equipment $E_1$ in FIG. 4 as an example, the ratio $R_{1'}$ of the CT equipment $E_1$ is very close to the critical value 81%, which indicates that the high contrast resolution for the CT equipment $E_1$ is certainly between the high contrast resolution $C_1$ and the high contrast resolution $C_{1'}$, and more close to the high contrast resolution $C_{1'}$.

(3) Further Definition of Normalized Margin

The concept of normalized margin (N) is further defined in order to improve the accuracy of measurement results and enable measurement results to be accurate at the decimal level just like MTF under the premise of ensuring the effectiveness: N=M/D, where distance D=R′−R″, wherein M is the margin;

R″ is the first ratio;

R′ is a second ratio on the R curve for the CT equipment that is just above 80%.

Step 4, Comparative Assessment (1) In the case that the high contrast resolutions of line pair groups corresponding to the last ratios R below 80% in different ratio R curves, the normalized margins corresponding to the integer-level high contrast resolutions are compared. The larger the value of the normalized margin, the higher the high contrast resolution of the line pair group.

When the $margin_{E1}$ of the CT equipment $E_1$ is equal to 80%-$R_1$, and $distance_{E1}$ is equal to $R_1$-$R_1$, the high contrast resolution $C_{E1}$ for the CT equipment $E_1$ is equal to $C_1+N_{E1}$. Because the normalized margin is a value between 0 and 1, a greater value represents that the high contrast resolution is closer to $(C_1+1)$LP/cm.

For the CT equipment $E_2$, the high contrast resolution $C_2$ corresponding to the last pixel intensity profile ratio $R_2$ below 81% is equal to 4LP/cm according to the Rayleigh criterion. The $margin_{E2}$ is equal to 80%-$R_2$ and it is not zero, and the high contrast resolution for the CT equipment $E_2$ is between the high contrast resolution $C_2$ and the high contrast resolution $C_{2'}$; similarly, the normalized margin $N_{E2}$ for the CT equipment $E_2$ is equal to $margin_{E2}/distance_{E2}$; then, the high contrast resolution $C_{E2}$ for the CT equipment $E_2$ is equal to $C_2+N_{E2}$.

(2) When the high contrast resolutions of two pieces of equipment are at the same integer level, more detailed comparison can be made by comparing the normalized margins of the two pieces of equipment at this integer level; the larger the normalized margin, the higher the high contrast resolution.

(3) If the two pieces of equipment have their normalized margins very close to each other at the same high contrast resolution level, comparison needs to be made to the area defined by the ratio R, the last ratio R below 80% and the high contrast resolution C of each equipment; the larger the area, the worse the high contrast resolution.

In this embodiment, calculation is simplified to only the last ratio R below 80% and the first ratio R of 80% or above.

A specific operating method for a tester is described below.

The tester performs interpolation to an image of the high contrast resolution module in a CT phantom to be tested using image processing tool software having the interpolation processing and regional pixel intensity profile functions. After the interpolation, the tester readily finds out the region of the high contrast resolution through visual inspection. Generally, the high contrast resolution is typically located between two line pair groups, i.e., the last line pair group that can be distinguished as being not sticking, connected and broken through visual inspection by adjusting a window width (WW) and a window level (WL), and the first line pair group that cannot be distinguished through visual inspection. It is above 90% possibility that the regional pixel intensity profile is just continuously created for the two line pair groups using commercial image processing tool software and corresponding ratios R are calculated; if the ratios R of the two line pair groups do not satisfy the use condition as described above, it only needs to create the regional pixel intensity profile for one more line pair group. Because high uncertainty is present in visual assessment and it is possible that visually distinguishable line pair groups are not distinguishable objectively sometimes, the regional pixel intensity profile needs to be created for one more line pair group sometimes. In short, the regional pixel intensity profile is created for at most three line pair groups.

Then, the normalized margin is calculated according to the above method, thus obtaining the final high contrast resolution that can be made accurate to the decimal level.

Finally, the tester makes assessment according to the high contrast resolution result: the high contrast resolution of the line pair groups corresponding to the last ratios R below 80% among different ratios R are compared; the larger the value of the line pair group, the higher the high contrast resolution.

If two pieces of equipment are identical in the high contrast resolution of the line pair group corresponding to the last ratio R below 80%, the normalized margins corresponding to the two ratios R may be compared; the larger the normalized margin, the higher the high contrast resolution for the CT equipment.

If two pieces of equipment have their normalized margins very close to each other at the same high contrast resolution level, comparison needs to be made to the area defined by the ratio R, the last ratio R below 80% and the high contrast resolution of each equipment; the larger the area, the worse the high contrast resolution.

In short, the present invention has the accuracy and reproducibility in the same level as the modulation transfer function (MTF) method, but is far better than the MTF method in operability and detection efficiency.

Figure 5:
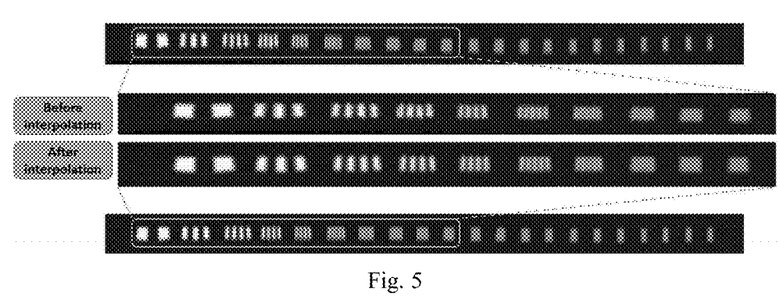
FIG. 5 shows comparison of CT equipment A before and after interpolation to a high contrast resolution image.
Figure 6:
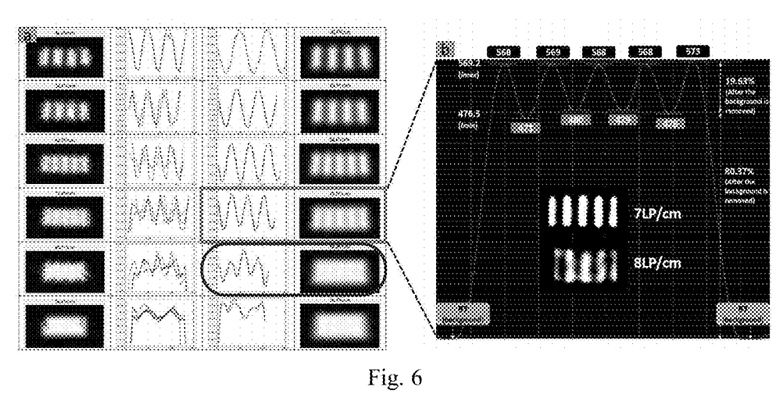
FIG. 6 is a schematic diagram of comparison of CT equipment A before and after interpolation to a high contrast resolution image under conditions of 120 kV-300 mAs-5 mm.
Figure 7:
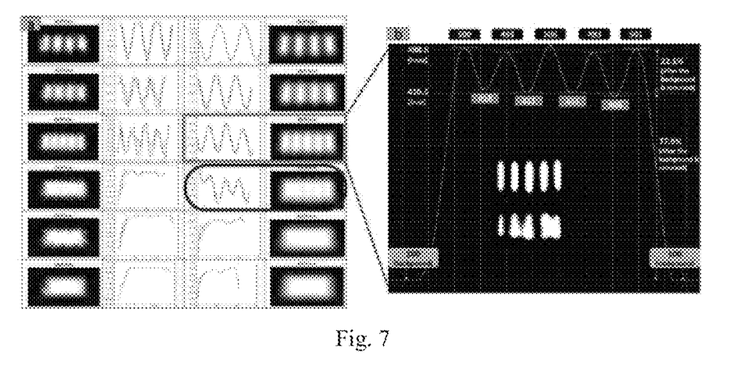
FIG. 7 is a schematic diagram of comparison of CT equipment B before and after interpolation to a high contrast resolution image under conditions of 120 kV-300 mAs-5 mm.
Figure 8:
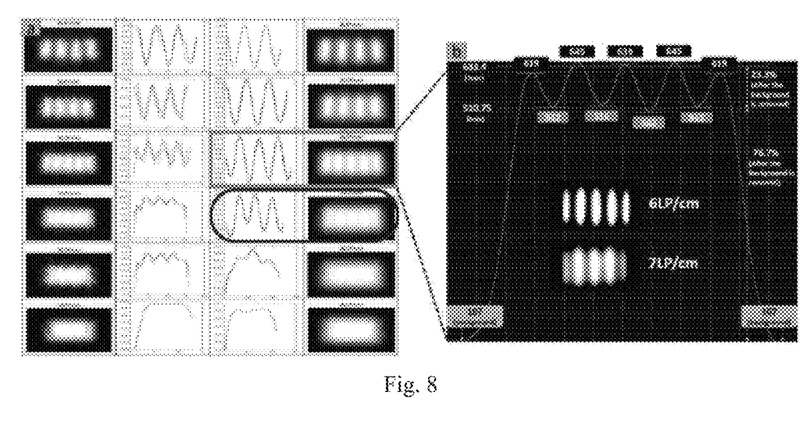
FIG. 8 is a schematic diagram of comparison of CT equipment C before and after interpolation to a high contrast resolution image under conditions of 120 kV-300 mAs-5 mm.

As shown in FIG. 5, by taking CT equipment A as an example, the image size after interpolation is set to 2048×2048 by using the Lanczos method. Image comparison results before and after interpolation are as shown in FIG. 5.

As can be seen clearly from an straightened image, after the interpolation processing using the Lanczos algorithm, it seems from visual inspection that the image quality of the region of interest (ROI) of the high contrast resolution is obviously improved; besides, the interpolation method may cause the internal and external boundaries of the line pair groups to become clear and smooth while guaranteeing the distortionless image. The comparison of the middle three lines of the regional pixel intensity profiles of (4-9) LP/cm line pair groups of three pieces of CT equipment before and after interpolation is as shown in FIG. 6(a), FIG. 7(a), and FIG. 8(a).

For single CT equipment, the overlapping of the adjacent pixel points of the internal and boundary parts of each line pair group is also greatly improved; the internal and external boundaries of the line pair groups become quite smooth; 6 LP/cm or 7 LP/cm line pair groups that can only be seen clearly by continuously adjusting the window width (WW) and the window level (WL) may be distinguished readily in the interpolated image. As shown in FIG. 6(b), FIG. 7(b), and FIG. 8(b), visually, CT equipment A still has certain high contrast resolution at 8 LP/cm, whereas this resolution is already unable to completely show all information of the line pair groups; the images of the aluminum strips have deformations at different degrees with certain local sticking. CT equipment B has poor resolution capability at 7 LP/cm with severe deformation and sticking. For CT equipment C at 7 LP/cm, the information of the middle three aluminum strips is apparent with severe decline in the external boundary parts and sticking in whole.

After an image is subjected to the interpolation processing, the consistency of the regional pixel intensity profiles in middle three lines of each line pair group is greatly improved, and the regional pixel intensity profile in a certain middle line is judged by using this embodiment. As shown in FIG. 6(b), FIG. 7(b), and FIG. 8(b), the last line pair groups having the ratios R not above 80% of the minimum pixel intensity $I_{min}$ to the maximum pixel intensity $I_{max}$ of the three pieces of equipment are 7 LP/cm for CT equipment A, 6 LP/cm for CT equipment B and 6 LP/cm for CT equipment C, respectively, and the ratios R of the CT equipment A, the CT equipment B and the CT equipment C are 80.37%, 77.9% and 76.7%, respectively.

As shown in FIG. 6(b), the ratio R of the CT equipment A at 7 LP/cm for the equipment is very close to the critical value 81%. A volunteer group (including 5 junior QA (Quality Assessment) testers lacking experience) and an expert group (including 3 professionals in the field of medical image quality assessment (QA)) are invited as testers to assess 7 LP/cm line pair groups in an image from the CT equipment A, 6 LP/cm line pair groups in an image from the CT equipment B, 6 LP/cm line pair groups in an image from the CT equipment C and 6 LP/cm line pair groups in an image from the CT equipment A by using the present invention. The internal middle position in each line pair group is selected as far as possible for the regional pixel intensity profile. Each tester makes one-time regional pixel intensity profile assessment based on the Rayleigh criterion on each image. In the whole process, the testers do not interfere with each other. The assessment results obtained by the volunteer group and the expert group are averaged, and the experimental standard deviation s of single measurement is calculated, with results as shown in FIG. 9.

Figure 9:
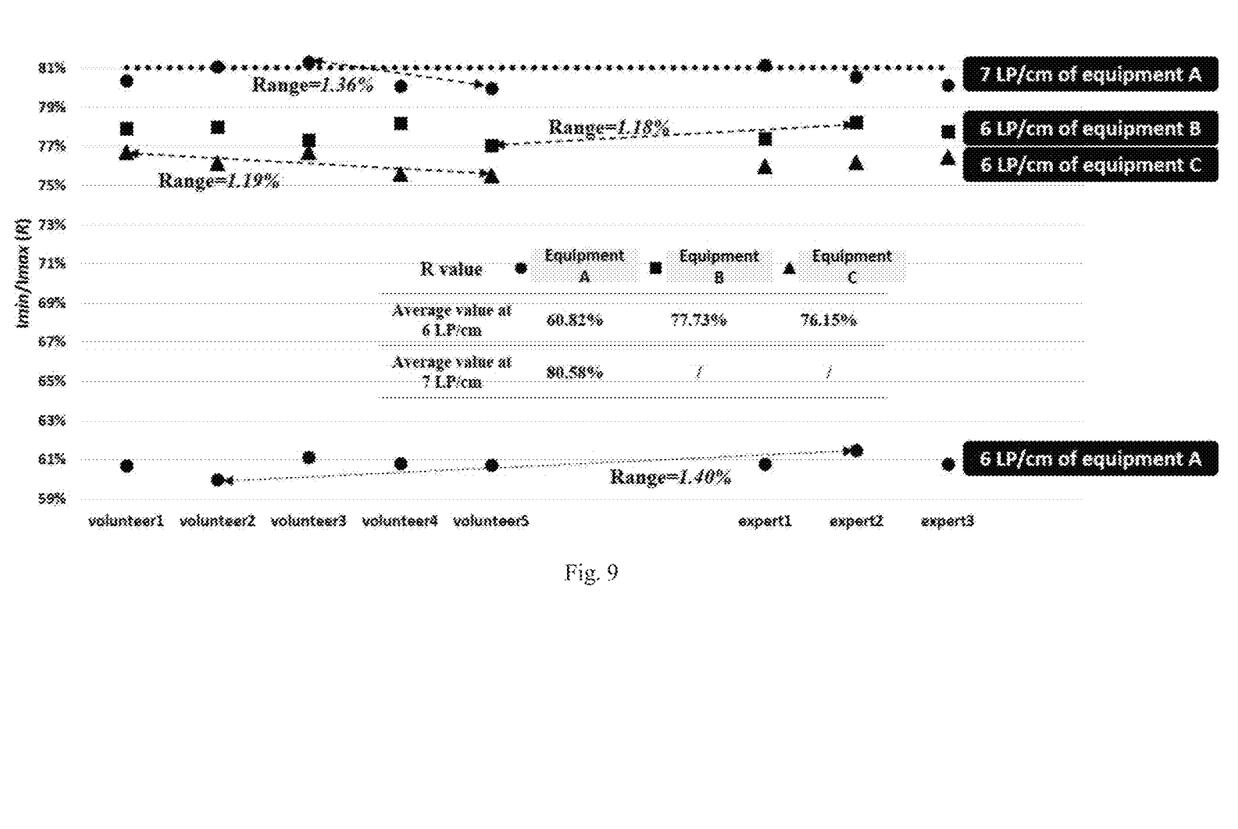
FIG. 9 is a schematic diagram of assessment results obtained by a volunteer group and an expert group on regional pixel intensity profiles of three pieces of equipment on the basis of the Rayleigh criterion.

Firstly, as can be seen from FIG. 9, the measurement results obtained by the volunteer group and the expert group are almost completely the same. Therefore, this test can be regarded as a set of 8 repeated tests. The ranges of four sets of data measurements, namely the difference between the maximum and the minimum among n measurement results in the repeated measurement, are 1.36%, 1.18%, 1.19% and 1.40%. According to the definition of the range, the experimental standard deviation s of the single measurement result is expressed as:

$$s = \frac{\text{range}}{F}$$

In the above formula, F is a range coefficient. Through table look-up, when the number of the measurement times is 8, the range coefficient F is 2.85; it thus can be obtained that the experimental standard deviations s of single measurement among 4 sets of data are 0.477%, 0.414%, 0.417% and 0.491%, respectively. This indicates that the regional pixel intensity profile method has excellent reproducibility from another angle. The above measurement results all conform to normal distribution, and according to the statistical experience, about 95% of measurements may fall within the interval of (average values±2s). The maximum experimental standard deviation of single measurement among the above four sets of data is 0.491%, and 2s is equal to 0.982% (<1%). That is, 95% results of any measurement on the regional pixel intensity profile of a certain line pair group fall into the interval of (average value±1%). Since the present invention has good reproducibility, according to FIG. 4, the ratio R curves of (1-10) LP/cm for images of 3 pieces of equipment are drawn up, as shown in FIG. 10.

Proved by a lot of experiments, such a novel objective assessment method can be further simplified in the overwhelming majority of cases. That is, the normalized margin is the core parameter of the high contrast resolution, and the acquisition of this value only depends on the last ratio R below 80% and the first ratio R of 80% or above in a ratio R curve; or, the ratio R curve does not need to be drawn up in the overwhelming majority of cases, and instead, two key ratios R are just calculated to obtain an accurate high contrast resolution testing result.

In the present invention, because the Lanczos interpolation algorithm is embedded in most commercial image analysis software, only simple interpolation processing needs to be performed on an original high contrast resolution image to well satisfy the use condition of the Rayleigh criterion. The regional pixel intensity profile is also a very common image analysis function.

Figure 10:
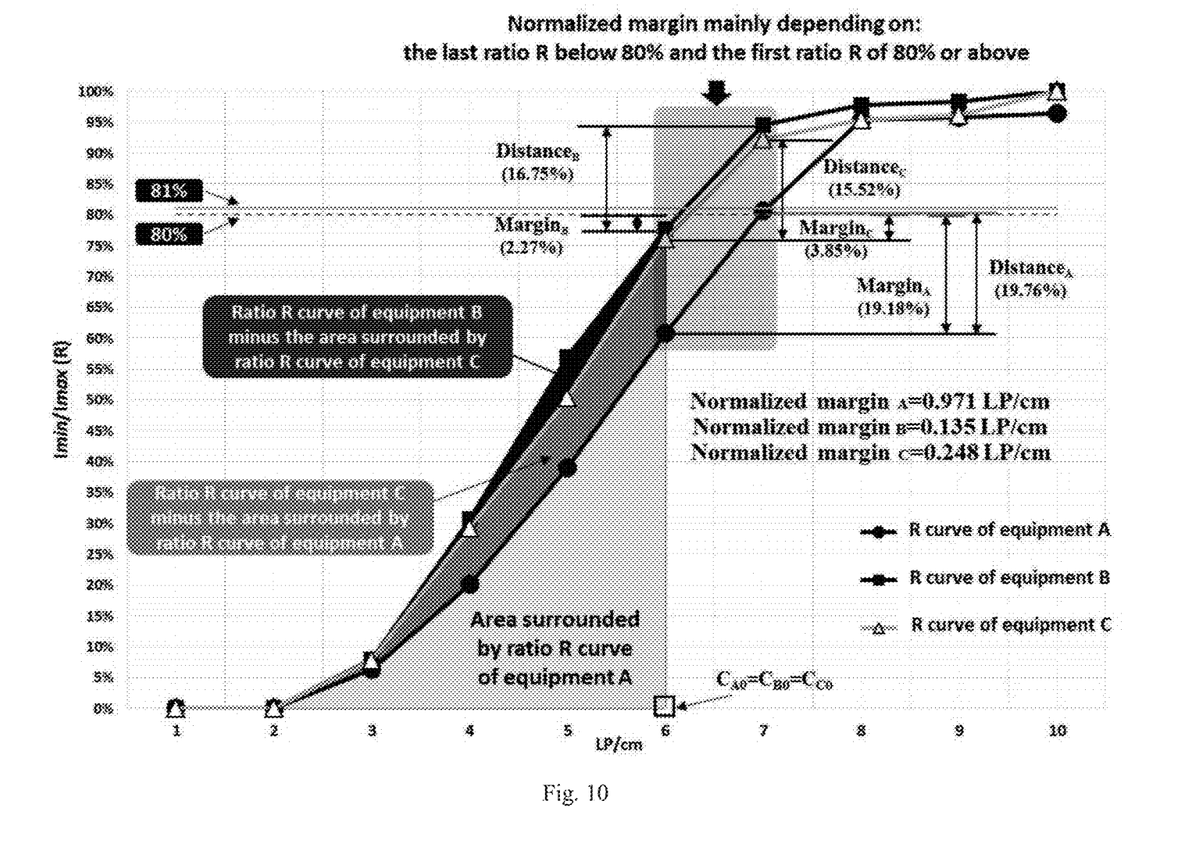
FIG. 10 is a schematic diagram of further quantifying assessment results of the Rayleigh criterion on three pieces of equipment using a normalized margin.

FIG. 10 further illustrates the assessment features of the present invention: (1) comparison is made to the high contrast resolution of the line pair group corresponding to the last ratio R below 80% in each of different R curves; the larger the value of the line pair group, the higher the resolution capability; (2) if two pieces of equipment have the same high contrast resolution of the line pair group corresponding to the last ratio R below 80%, comparison may be made to the normalized margins corresponding to the two ratios R; the larger the normalized margin, the higher the high contrast resolution of the equipment; (3) if two pieces of equipment have their normalized margins very close to each other at the same cutoff frequency level, comparison needs to be made to the area defined by the ratio R, the last ratio R below 80% and the high contrast resolution of each equipment; the larger the area, the worse the high contrast resolution.

Proved by a lot of experiments: for a certain piece of CT equipment, the testing results may not be heavily affected by the change of such scanning parameters as tube current and tube voltage under the conditions of invariable field of view (FOV), slice thickness and reconstruction algorithm, and do not exhibit a very obvious law with the change of the tube current and the tube voltage. Hence, the set of common scanning conditions of 120 kV, 300 mAs and 5 mm was utilized in all of the experiments.

Summary and comparison are made to the visual inspection assessment results of the volunteer group and the expert group with regard to 120 kV-300 mAs-5 mm images of three pieces of equipment.

In clinical application, MTF=10% (threshold $MTF_{10\%}$) reflects the resolution of CT equipment to skeletons, and the aluminum line pair groups in the CTP528 module are quite close to the CT values of skeletons; moreover, Report No. AAPM39 (technical report No. 39 of American Association of Physicists in Medicine) also recommends the horizontal coordinate value, which corresponds to the intersection point of the MTF curve and the threshold $MTF_{10}\%$, as the visual resolution. Hence, a volunteer group and an expert group are also invited as testers to perform MTF assessment on high contrast resolution images of CT equipment A, CT equipment B and CT equipment C under the condition of 120 kV, 300 mAs and 5 mm slice thickness. Each tester makes one-time assessment on each image. The experimental standard deviation s of single measurement is calculated according to the following formula (1).

Independent measurement is performed on the measured X for n times under reproducibility conditions, and then the experimental standard deviation s of a single measurement result $x_k$ is as follows:

$$s = \sqrt{\frac{\sum_{k=1}^{n}(x_k - \bar{x})^2}{(n-1)}} = u(x_k), \qquad (11)$$

where $\bar{x}$ is an average value of n-time independent measurement results; $u(x_k)$ is the standard uncertainty of a single measurement result $x_k$.

If independent observation is performed on the measured for n times under reproducibility conditions, measurement results $x_{i1}, x_{i2}, \ldots x_{in}$, and an average value $\bar{x}_i$ are obtained.

If there are m observers performing such measurement, a pooled estimate of standard deviation $s_p$ is used for statistical analysis:

$$s_p = \sqrt{\frac{\sum_{i=1}^{m}\sum_{j=1}^{n}(x_{ij}-\overline{x}_t)^2}{m(n-1)}} = u(x_j). \quad (2)$$

Figure 11:
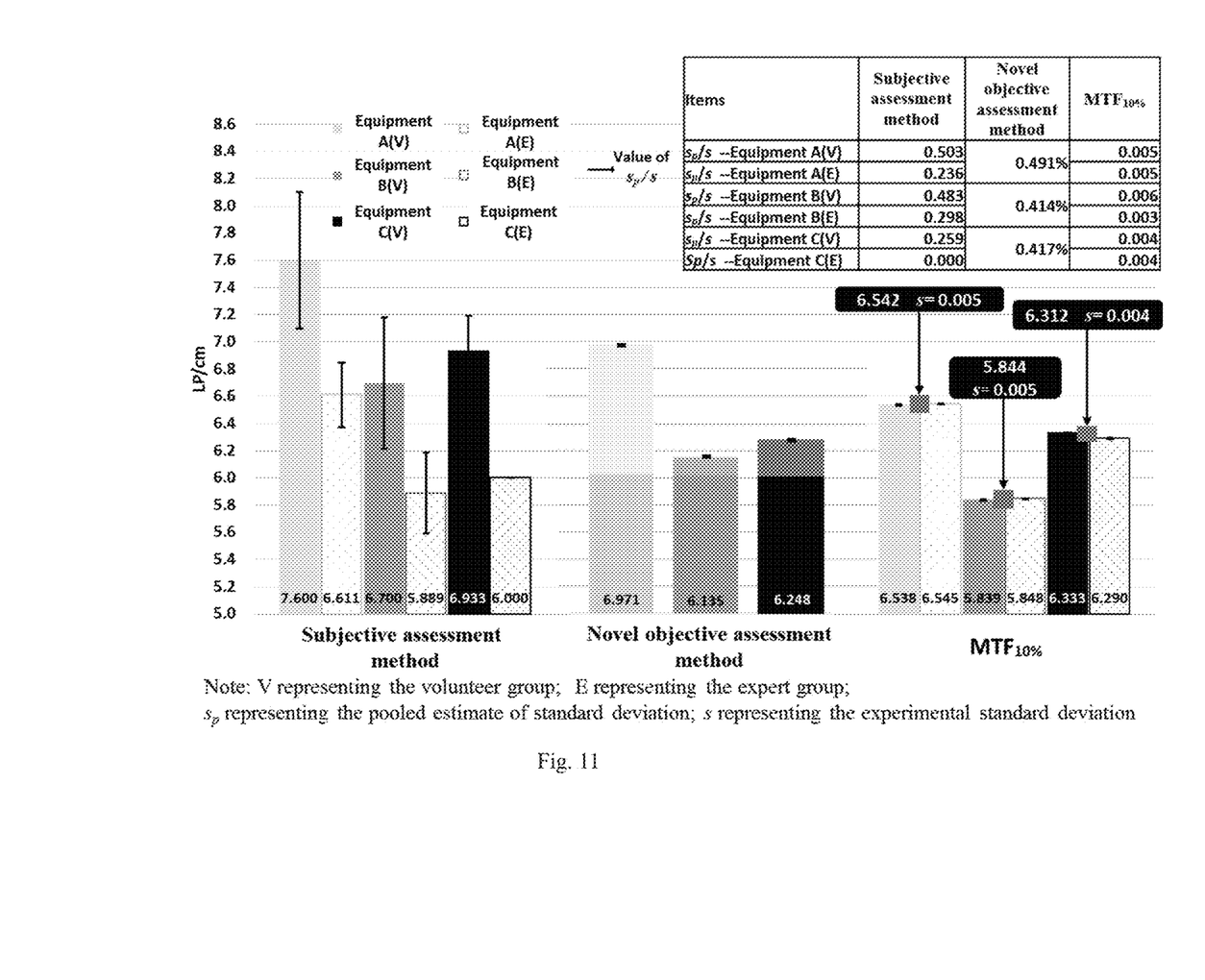
FIG. 11 is a schematic diagram of summary of results of various assessment methods for high contrast resolution images of three pieces of equipment (120 kV-300 mAs-5 mm).

As shown in FIG. 11, summary is made to the results of the foregoing subjective assessment, the MTF assessment and the assessment of the present invention. The assessment results of the volunteer group and the expert group on three pieces of equipment are arranged for each assessment method, and the pooled estimates of standard deviation $s_p$ or the experimental standard deviations s of all the assessment results are also listed in the form of table. According to the data in FIG. 11, the MTF assessment on each equipment is also regarded as a set of 8 repeated tests; then, the total average values of the objective assessment on CT equipment A, CT equipment B and CT equipment C and corresponding experimental standard deviations s are respectively as follows: 6.542 LP/cm (s=0.005 LP/cm), 5.844 LP/cm (s=0.005 LP/cm), 6.312 LP/cm (s=0.004 LP/cm).

The following results are obtained from FIG. 11, the pooled estimate of standard deviation $s_p$ of the subjective assessment method is within the range of (0.2-0.6) LP/cm, and it is almost present in each measurement; however, the uncertainty of the expert group is obviously lower than that of the volunteer group. The experimental standard deviation s of the single measurement result of the MTF assessment method is not higher than 0.006, which can almost be neglected; therefore, the MTF assessment method has good reproducibility. The present invention has a very small single experimental standard deviation s in the regional pixel intensity profile measurement process, which is not higher than 0.5%, and thus also has good reproducibility. Besides, when the MTF assessment method and the assessment method of the present invention are used, the assessment results of the volunteer group and the expert group are very close, thereby completely satisfying multiple repeated measurement.

Figure 12:
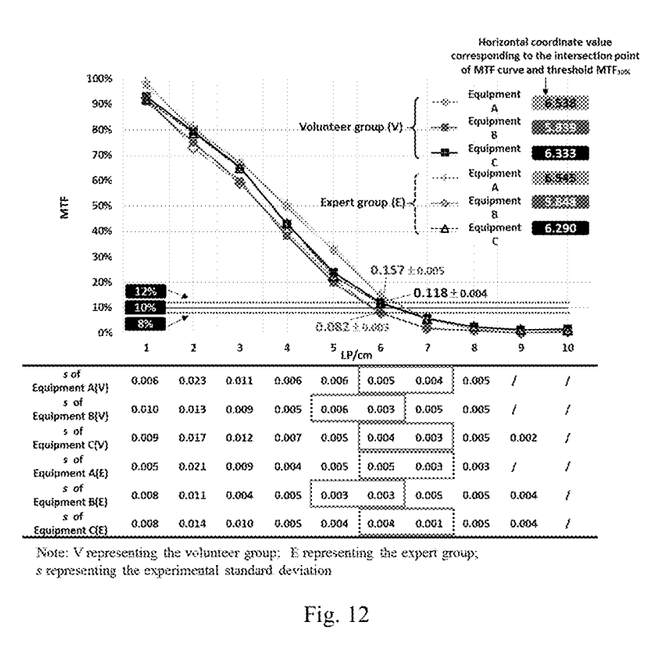
FIG. 12 shows comparison of MTF curves of three pieces of CT equipment.

In the objective assessment on CT equipment B and CT equipment C, the high contrast resolutions corresponding to the threshold $MTF_{10\%}$ are 5.844 LP/cm and 6.312 LP/cm, which can both be accepted as 6 LP/cm magnitude. Referring to FIG. 12, the MTF values in the MTF curves corresponding to 6 LP/cm in two images of the CT equipment B/the CT equipment C are (0.082±0.003) and (0.118±0.004), which are very close to the threshold $MTF_{10\%}$. Accordingly, although the assessment results on the two pieces of equipment by using the present invention are located on the two sides of 6 LP/cm, the deviations are very small; therefore, it can be regarded that the high contrast resolution capabilities of the CT equipment B and the CT equipment C are approximate to 6 LP/cm. Hence, the assessment results of the MTF method are consistent with those of the present invention, and comply with the standard provisions.

Besides, for the MTF assessment method, the threshold $MTF_{10\%}$ is just a reference index in high contrast resolution assessment, but more often, comparison made to high contrast resolution depends on the slope of the MTF curve and the area covered by the MTF curve. In the present invention, a whole ratio R curve is hardly needed; instead, it only needs to find two ratios R: the last ratio below 80% and the first ratio of 80% or above, and only the normalized margin needs to be calculated to obtain the assessment result on the high contrast resolution simply and accurately. Besides, the decimal place in the decimal-level assessment result is meaningful, which can substantially represent the resolution level of the equipment.

In short, the present invention is highly consistent with the objective assessment in results. Furthermore, the present invention has the time efficiency of the subjective method and the accuracy and reproducibility of the MTF method. Under the circumstance of difficult operation of the MTF assessment method, such a simple and convenient objective assessment method can completely meet the testing requirements on the high contrast resolution in QA for medical CT equipment, and can also greatly improve the working efficiency of QA workers for medical equipment.

The forgoing descriptions are merely preferred embodiments of the present invention, rather than limiting the present invention in any form. While the preferred embodiments are described above to illustrate the present invention, they are not intended to limit the present invention. Any person skilled in the art can make some alterations or modifications by using the above disclosed technical contents without departing from the scope of the technical solutions of the present invention to obtain equivalent embodiments. Any content not departing from the technical solutions of the present invention and any simple alternation, equivalent variation and modification made to the above embodiments according to the technical essence of the present invention all still fall into the scope of the technical solutions of the present invention.

What is claimed is:

1. A method for assessing high contrast resolution of images by CT equipment based on Rayleigh criterion, comprising:
    applying an interpolation algorithm on an original image to clarify overlap of adjacent pixels and improve consistency of pixel intensity of three middle lines in the pixel intensity profile for each line pair group while ensuring preservation of complete information of the original image;
    subtracting an epoxy background value from the regional pixel intensity profile of each line pair group to avoid interference and determining a minimum pixel intensity value and a maximum pixel intensity value in the resulting regional pixel intensity profile;
    calculating a ratio R between the minimum pixel intensity value and the maximum pixel intensity value;
    determining that the line pair group is distinguishable if R≤81% and that the line pair group is indistinguishable if R>81%; and
    assessing high contrast resolution of images by the CT equipment based on whether the line pair group is determined to be distinguishable.

2. The method of claim 1, further comprising:
    determining a margin, M=80%−R", where R" is the last measured ratio on a R curve for the CT equipment that is lower than 80%, the R curve obtained by calculating ratios between minimum pixel intensity values and maximum pixel intensity values for images obtained for a predetermined sequence of line pair groups;
    determining a distance, D=R'−R", where R' is the first measured ratio on the R curve for the CT equipment that is higher than 80%;
    determining a normalized margin, N=M/D;
    assessing high contrast resolution of images by the CT equipment based on the normalized margin.

3. A method of comparing high contrast resolution of images by two pieces of CT equipment, comprising:
assessing high contrast resolution of images by each of the two pieces of CT equipment in accordance with the method of claim 2; and
comparing high contrast resolution of images by the two pieces of CT equipment by comparing the normalized margins for the two pieces of CT equipment.

4. The method of claim 3, wherein when the normalized margins for two pieces of CT equipment are substantially identical, compare high contrast resolution of images by the two pieces of CT equipment by comparing areas defined by the R curve, a horizontal axis of the coordination system, and a vertical line passing through a first point representing the last measured ratio on the R curve that is lower than 80% for each of the two pieces of CT equipment.

5. A novel objective method for assessing high contrast resolution of images based on Rayleigh criterion, comprising the following steps:
Step 1: a regional pixel intensity profile method based on the Rayleigh criterion the Rayleigh criterion is combined with a regional pixel intensity profile for simultaneous application to a high contrast resolution image of CT equipment, wherein objective assessment is carried out using the Rayleigh criterion after the drawing of regional pixel intensity profiles, i.e., judging a line pair group resolution capability by visually inspecting the shape fluctuation of the regional pixel intensity profiles of regions of interest (ROIs), followed by the objective assessment by using the Rayleigh criterion; a basic method of the Rayleigh criterion is that when two diffraction fringes formed by two point light sources on an image plane of an optical instrument are combined into a wide fringe, the two fringes are just distinguishable from each other when an irradiance at the center of the wide fringe or a lowest amplitude is $8/\pi^2$ (i.e., 0.81)×a maximum irradiance;

Step 2: interpolation processing on an original image
the use of an interpolation algorithm allows great improvement of overlapping of original adjacent pixel points and enhancement of the consistency of middle three lines of pixel intensity profiles in each line pair group under the circumstance of ensuring complete information of the original image;

Step 3: definition of normalized margin
(1) determination of ratio R
although the use condition for the Rayleigh criterion is two isolated point light sources equivalent in intensity, each aluminum strip through which the regional pixel intensity profile passes can be also viewed as a point source due to very small size of the line pair groups and the regional pixel intensity profile reflecting the local information of each line pair group; Since most line pair groups are each composed of 4 or 5 line pairs, for the regional pixel intensity profile of a certain line pair group, the epoxy background having a CT (computed tomography) number of about (100-120) HU needs to be subtracted to avoid interference; therefore, the minimum pixel intensity and the maximum pixel intensity are equal to the average amplitude of these line pairs minus the background; in other words, when the ratio R of the minimum pixel intensity to the maximum pixel intensity is not above 81%, the line pair group is regarded as being distinguishable;

(2) definition of margin
when the ratio R=the minimum pixel intensity ÷ the maximum pixel intensity is close to 81% and the assessment result is at the integer level, it is necessary to define the margin: M=80%−R",
wherein M is the margin;
R" is a first ratio on a R curve for the CT equipment that is just below 80%;
CT equipment $E_1$ and CT equipment $E_2$ with significant differences in high contrast resolution capability are selected, and the ratios R of (1-10) LP groups of the CT equipment $E_1$ and the CT equipment $E_2$ were connected into piecewise lines, defined as ratio $R_1$ and ratio $R_2$, respectively; the ratio R being between 80% and 81% indicates that the high contrast resolution for a certain piece of equipment is between two adjacent line pair groups; the ratio of the CT equipment $E_1$ is very close to the critical value 81%, which indicates that the high contrast resolution for the CT equipment $E_1$ is certainly between the high contrast resolution $C_1$ and the high contrast resolution $C_{1'}$ and more close to the high contrast resolution $C_{1'}$;

(3) further definition of normalized margin
the normalized margin is further defined in order to improve the accuracy of measurement results, i.e., to enable measurement results to be accurate at the decimal level just like the MTF method under the premise of ensuring the effectiveness: N=M/D, where distance D=R'−R", wherein M is the margin;
R" is the first ratio;
R' is a second ratio on the R curve for the CT equipment that is just above 80%;

Step 4: comparative assessment
(1) in the case that the high contrast resolutions C of line pair groups corresponding to the last ratios R below 80% in different ratio R curves are the same, the normalized margins N corresponding to the integer-level high contrast resolutions C are compared; the larger the value of the normalized margin, the higher the high contrast resolution C for the CT equipment; when the margin$_{E1}$ of the CT equipment $E_1$ is equal to 80%−$R_1$, and the distance$_{E1}$ is equal to $R_1$-−$R_1$, then the normalized margin $N_{E1}$ of the CT equipment $E_1$ is equal to margin$_{E1}$d distance$_{E1}$, thus the high contrast resolution $C_{E1}$ for the CT equipment $E_1$ is equal to $C_1+N_{E1}$; Because the normalized margin is a value between 0 and 1, a greater value represents that the high contrast resolution for the CT equipment $E_1$ is closer to ($C_1$+1) LP/cm;
for the CT equipment $E_2$, the high contrast resolution $C_2$ corresponding to the last pixel intensity profile ratio $R_2$ below 81% is equal to 4LP/cm according to the Rayleigh criterion; the margin$_{E2}$ is equal to 80%−$R_2$ and it is not zero, and the high contrast resolution for the CT equipment $E_2$ is between the high contrast resolution $C_2$ and the high contrast resolution $C_{2'}$; similarly, the normalized margin $N_{E2}$ of the CT equipment $E_2$ is equal to margin$_{E2}$/distance$_{E2}$; then, the high contrast resolution $C_{E2}$ for the CT equipment $E_2$ is equal to $C_2+N_{E2}$;

(2) when the high contrast resolutions of two pieces of equipment are at the same integer level, more detailed comparison can be made by comparing the normalized margins of the two pieces of equipment at this integer level; the larger the normalized margin, the better the high contrast resolution for the CT equipment;

(3) if the two pieces of equipment have their normalized margins very close to each other at the same high contrast resolution level, comparison needs to be made to the area defined by the ratio R curve, the last ratio R below 80% and the high contrast resolution C for each equipment; the larger the area, the worse the high contrast resolution.

6. The method according to claim 1, wherein the interpolation is performed using a Lanczos window function for interpolation processing on the original image.

7. The method according to claim 5, wherein the step (4) is simplified to calculate only a last ratio R below 80% and a first ratio R of 80% or above.

8. A testing operating method on CT equipment according to the novel objective method for assessing high contrast resolution of images based on Rayleigh criterion of claim 5, further comprising the following steps:

Step 1: interpolation processing
a tester performs interpolation processing on a high contrast resolution image of CT equipment to be tested using image processing tool software having the interpolation processing and regional pixel intensity profile functions;

Step 2: visual inspection distinguishing
after the interpolation, the tester finds out the region of the high contrast resolution through visual inspection; the last line pair group that can be clearly distinguished as being not sticking, connected and broken through visual inspection by adjusting a window width (WW) and a window level (WL), and the first line pair group that cannot be distinguished through visual inspection; it is above 90% possibility that only the regional pixel intensity profile assessment based on Rayleigh criterion needs to be continuously made for the two line pair groups using commercial image processing tool software and corresponding ratios R are calculated; if the ratios R of the two line pair groups do not satisfy the use condition as described above, it only needs to make the regional pixel intensity profile assessment based on Rayleigh criterion for one more line pair group;

Step 3: calculation of normalized margin
the tester calculates the normalized margin according to the normalized margin formula in step 3 of claim 1 to obtain the final high contrast resolution that can be accurate to the decimal level;

Step 4: comparative assessment
the tester makes comparative assessment according to the method in step 4 of claim 1.

9. An apparatus for assessing quality of medical equipment, said apparatus including a processor and memory for performing the method of claim 5.

10. A non-transitory computer-readable medium containing a computer program which, when executed by a computer, results in the computer performing the method of claim 1.

11. The method according to claim 2, wherein the interpolation is performed using a Lanczos window function for interpolation processing on the original image.

12. The method according to claim 3, wherein the interpolation is performed using a Lanczos window function for interpolation processing on the original image.

13. The method according to claim 4, wherein the interpolation is performed using a Lanczos window function for interpolation processing on the original image.

14. The method according to claim 5, wherein the interpolation is performed using a Lanczos window function for interpolation processing on the original image.

15. A testing operating method on CT equipment according to the novel objective method for assessing high contrast resolution of images based on Rayleigh criterion of claim 6, further comprising the following steps:

Step 1: interpolation processing
a tester performs interpolation processing on a high contrast resolution image of CT equipment to be tested using image processing tool software having the interpolation processing and regional pixel intensity profile functions;

Step 2: visual inspection distinguishing
after the interpolation, the tester finds out the region of the high contrast resolution through visual inspection; the last line pair group that can be clearly distinguished as being not sticking, connected and broken through visual inspection by adjusting a window width (WW) and a window level (WL), and the first line pair group that cannot be distinguished through visual inspection; it is above 90% possibility that only the regional pixel intensity profile assessment based on Rayleigh criterion needs to be continuously made for the two line pair groups using commercial image processing tool software and corresponding ratios R are calculated; if the ratios R of the two line pair groups do not satisfy the use condition as described above, it only needs to make the regional pixel intensity profile assessment based on Rayleigh criterion for one more line pair group;

Step 3: calculation of normalized margin
the tester calculates the normalized margin according to the normalized margin formula in step 3 of claim 1 to obtain the final high contrast resolution that can be accurate to the decimal level;

Step 4: comparative assessment
the tester makes comparative assessment according to the method in step 4 of claim 1.

16. A testing operating method on CT equipment according to the novel objective method for assessing high contrast resolution of images based on Rayleigh criterion of claim 14, further comprising the following steps:

Step 1: interpolation processing
a tester performs interpolation processing on a high contrast resolution image of CT equipment to be tested using image processing tool software having the interpolation processing and regional pixel intensity profile functions;

Step 2: visual inspection distinguishing
after the interpolation, the tester finds out the region of the high contrast resolution through visual inspection; the last line pair group that can be clearly distinguished as being not sticking, connected and broken through visual inspection by adjusting a window width (WW) and a window level (WL), and the first line pair group that cannot be distinguished through visual inspection; it is above 90% possibility that only the regional pixel intensity profile assessment based on Rayleigh criterion needs to be continuously made for the two line pair groups using commercial image processing tool software and corresponding ratios R are calculated; if the ratios R of the two line pair groups do not satisfy the use condition as described above, it only needs to make the regional pixel intensity profile assessment based on Rayleigh criterion for one more line pair group;

Step 3: calculation of normalized margin
the tester calculates the normalized margin according to the normalized margin formula in step 3 of claim 1 to obtain the final high contrast resolution that can be accurate to the decimal level;

Step 4: comparative assessment
the tester makes comparative assessment according to the method in step 4 of claim 1.

17. An apparatus for assessing quality of medical equipment, said apparatus including a processor and memory for performing the method of claim 6.

18. An apparatus for assessing quality of medical equipment, said apparatus including a processor and memory for performing the method of claim 14.

19. A computer-readable medium containing a non-transitory computer program which, when executed by a computer, results in the computer performing the method of claim 3.

20. A computer-readable medium containing a non-transitory computer program which, when executed by a computer, results in the computer performing the method of claim 6.

21. A computer-readable medium containing a non-transitory computer program which, when executed by a computer, results in the computer performing the method of claim 14.

* * * * *